United States Patent [19]

Salama

[11] Patent Number: 4,968,294
[45] Date of Patent: Nov. 6, 1990

[54] URINARY CONTROL VALVE AND METHOD OF USING SAME

[76] Inventor: Fouad A. Salama, 3220 Valley Ridge Ct., West Des Moines, Iowa 50265

[21] Appl. No.: 307,992

[22] Filed: Feb. 9, 1989

[51] Int. Cl.⁵ .............................................. A61F 2/02
[52] U.S. Cl. ............................ 600/30; 128/DIG. 25; 604/247; 251/342
[58] Field of Search ........................... 600/29–32; 604/34, 247; 128/830, 834, 842, 843, 885, 886, 887, DIG. 25; 251/342

[56] References Cited

U.S. PATENT DOCUMENTS

| | | |
|---|---|---|
| 274,447 | 3/1883 | Kennish . |
| 3,463,141 | 8/1969 | Mozolf .............................. 128/887 |
| 3,503,400 | 3/1970 | Osthagen et al. .......... 128/DIG. 25 |
| 3,707,957 | 1/1973 | Bucalo ............................. 128/843 |
| 3,731,670 | 5/1973 | Loe . |
| 3,758,073 | 9/1973 | Schulte ..................... 128/DIG. 25 |
| 3,768,102 | 10/1973 | Kwan-Gett et al. . |
| 4,457,299 | 7/1984 | Cornwell . |
| 4,587,954 | 5/1986 | Haber ......................... 128/DIG. 25 |
| 4,643,169 | 2/1987 | Koss et al. ................. 128/DIG. 25 |
| 4,822,333 | 4/1989 | Lavarenne ................ 128/DIG. 25 |
| 4,846,784 | 7/1989 | Haber ......................... 128/DIG. 25 |
| 4,932,938 | 6/1990 | Goldberg et al. .................... 604/247 |

FOREIGN PATENT DOCUMENTS

| | | |
|---|---|---|
| 948947 | 6/1947 | Canada ............................. 128/843 |
| 2600259 | 7/1976 | Fed. Rep. of Germany ... 128/DIG. 25 |
| 3421568 | 12/1985 | Fed. Rep. of Germany ... 128/DIG. 25 |

*Primary Examiner*—Stephen C. Pellegrino
*Assistant Examiner*—Ralph Lewis
*Attorney, Agent, or Firm*—Zarley, McKee, Thomte, Voorhees & Sease

[57] ABSTRACT

A silicone valve is placed in the orifice of the urethra. The valve tube includes a pair of blade valve elements which extend from the valve side wall forwardly and inwardly. The tube includes a bulb portion in the area of the valve elements to provide pressure cavities for urine to accumulate and apply pressure to the blade elements to maintain them normally closed. Pressure on the opposite sides of the tube walls will open the valve to flow of urine therethrough.

16 Claims, 2 Drawing Sheets

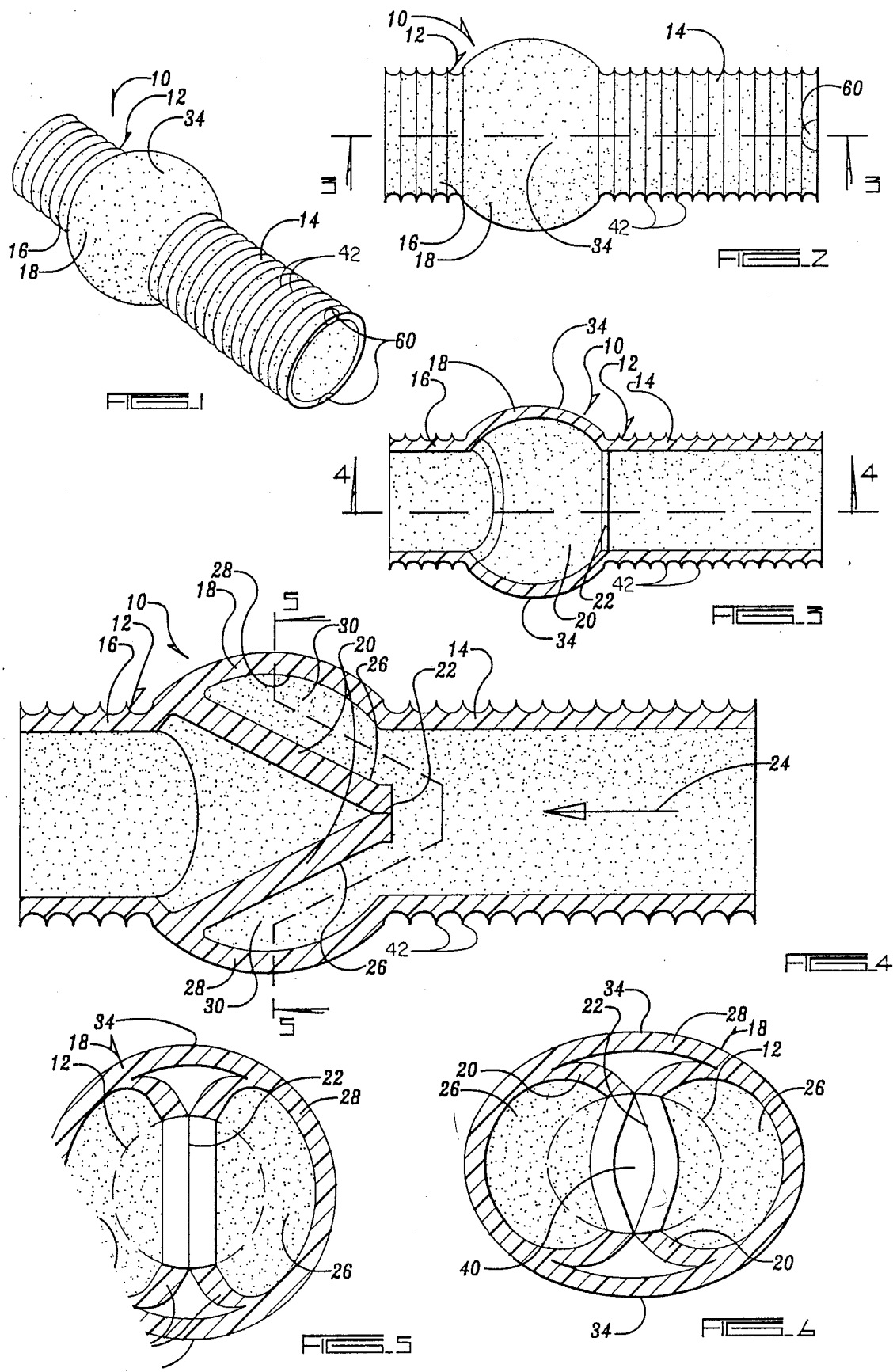

4,968,294

URINARY CONTROL VALVE AND METHOD OF USING SAME

BACKGROUND OF THE INVENTION

Incontinence is a problem for many people including older adults. Present day approaches to dealing with incontinence such as the Foley catheter often times causes urinary tract infection. A bag for urine is required and smell becomes a problem. The chances of infection are increased each time the bag is changed. The cost for the Foley catheters and pads is substantial.

What is needed is a simple inexpensive device for controlling urine flow in the urethra which is compatible to the body and will not cause discomfort or infection.

SUMMARY OF THE INVENTION

A disposable urethral valve of soft silicone material is placed in the orifice of the urethra. Oppositely disposed blade valve elements extend from the side walls of a tube laterally and longitudinally inwardly into engagement with each other in a normally closed position. The tube side walls are enlarged outwardly from the valve blade elements and their connection to the side walls thereby providing cavities between the blade elements and the side walls for urine to accumulate and build up pressure on the laid elements to keep them engaged and the valve closed. Pressure on the outside of the enlarged tube portion will spread the free ends of the blade elements and allow flow of urine from the bladder through the valve.

In the male, the entire valve is positioned in the orifice end of the urethra while in the female the enlarged bulb portion of the tube is disposed outwardly of the orifice in the labia majora such that access by the user's hand is possible for operation of the valve.

Serrations are provided on the outer tube side wall to increase the resistance to flow around the tube between the tube and the inside surface of the urethra.

In the male, the bulb or enlarged portion of the tube is positioned in the fossa navicularis and a portion of the tube extends outwardly to the end of the urethra.

Indica is provided on the opposite sides of the tube for orientation purposes such that it is known when it is inserted into the urethra where pressure needs to be applied to operate the valve. Ordinarily it would be positioned so pressure is applied on the top and bottom or on opposite sides. In the male, the pressure is applied to the opposite sides of the penis and will be transmitted to the opposite sides of the bulb in the tube for opening the valve. The pressure points on the bulb are in a plane extending through the interface plane of the blade elements.

DESCRIPTION OF THE DRAWINGS

FIG. 1 is a perspective view of the urinary control valve.

FIG. 2 is a side elevational view thereof.

FIG. 3 is a cross-sectional view taken along line 3—3 in FIG. 2.

FIG. 4 is an enlarged cross-sectional view taken along line 4—4 in FIG. 3.

FIG. 5 is a cross-sectional view taken along line 5—5 in FIG. 4 showing the valve in its normally closed position.

FIG. 6 is a cross-sectional view similar to FIG. 5, but showing the valve in its open position.

DESCRIPTION OF THE PREFERRED EMBODIMENT

Figure 7:
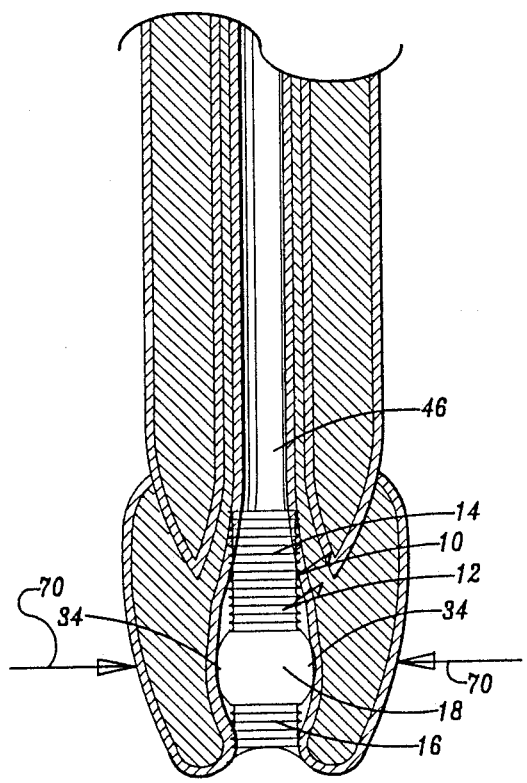
FIG. 7 is a fragmentary cross-sectional view of the valve in the orifice of the urethra in a male penis.

The urethra urinary control valve in this invention is referred to generally in FIG. 1 by the reference numeral 10 and includes an elongated tube 12 having a forward end, inlet tube portion 14 and a rear or outer end outlet tube portion 16 interconnected by an enlarged valved body bulb portion 18

In the enlarged bulb portion 18 are oppositely disposed wedge shaped blade valve elements 20 which are integral with the tube side wall and extend laterally inwardly and longitudinally forwardly as seen in FIG. 4. The blade elements 20 meet along their forward free ends along a straight line 22 to seal the tube against liquid flow from the right to the left as seen in FIG. 4 and indicated by the arrow 24. The blade elements 20 are substantially flat along at least their free ends to maximize the surface area 26 facing the inside tube wall surface 28 forming a cavity 30 between the blade elements 20 and the enlarged wall portion 28.

It is seen that urine in the forward tube portion 12 will fill the cavities 30 and apply pressure to the surface areas 26 of the blade elements 20 to maintain them in a closed position. Thus as they urine pressure increases, the pressure to keep the blade elements closed increases making for a foolproof valve.

The opening of the valve is accomplished by applying pressure on opposite sides of the bulb enlarged tube portion at pressure points 34 in a plane extending through the interface plane of the blade elements as seen in FIG. 5. This pressure will spread the free ends of the blade elements 20 apart to form a passageway 40 as seen in FIG. 6 whereby flow through the valve is possible.

Figure 8:
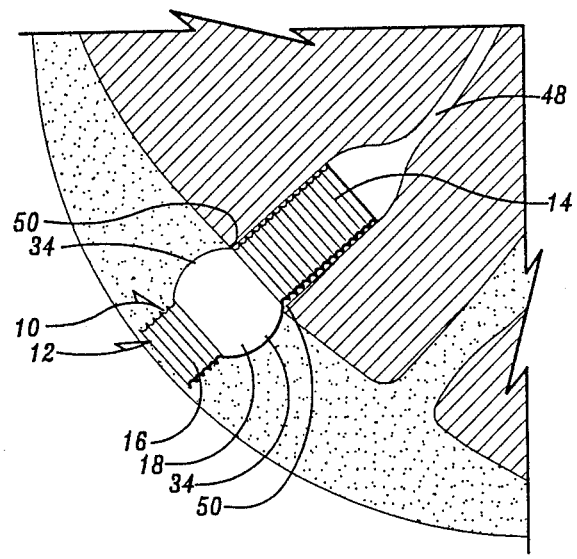
FIG. 8 is a fragmentary cross-sectional view of the valve in the orifice of the urethra in a female.

Annular serrations 42 are provided on the outside of the tube portions 14 and 16 and thus enhance the resistance to flow of urine around the outside of the tube between the tube and the inside surface of the wall of the urethra 46 as seen in FIG. 7 in the male and the urethra 48 in FIG. 8 in the female.

When used by the male as seen in FIG. 7, it is placed in the outlet orifice of the urethra such that the valved body bulb portion 18 is positioned in the fossa navicularis with the outer portion 16 extending outwardly to the distal end of the urethra.

When used by the female, the inner tube portion 14 is inserted into the orifice 50 of the urethra 48 up to the bulb portion 18 which along with the outer tube portion 16 is positioned in the labia majora where the valve is protected against unintended operation and is concealed against inadvertent contact with clothing and the like.

Thus in operation, it is seen that orientation indicia 60 is provided on the top and bottom surfaces of the tube portion 14 or in any other convenient location to indicate the relative position of the pressure points 34 such that when inserted the user will know where to apply pressure. Ordinarily the valve would be orientated so that pressure would be applied on the top and the bottom or on opposite sides. In the male, pressure is applied to the outside of the penis directly opposite the pressure points 34 as indicated by the arrows 70 in FIG. 7. This will cause the free ends of the blades 20 to spread apart as seen in FIG. 6 allowing urine flow through the passageway 40 formed by the spaced apart blades 20. In the female, as seen in FIG. 8, access is provided to the bulb 18 in the labia majora such that pressure may be applied to the pressure points 34 to open the valve. When pressure is removed the valve will normally close due to the memory of the elastomer silicone material. Elastomer silicone of a 50 or 55 durometer from Dow Corning, Midland, Mich., is recommended as it is compatible with the human body. While the valve may have varying dimensions to suit particular needs, it is suggested that it be three centimeters long with a 2 millimeter wall thickness for use in the typical urethra having a 6 millimeter internal diameter. A gel, such as Zylocain may be used for ease of inserting into the urethra.

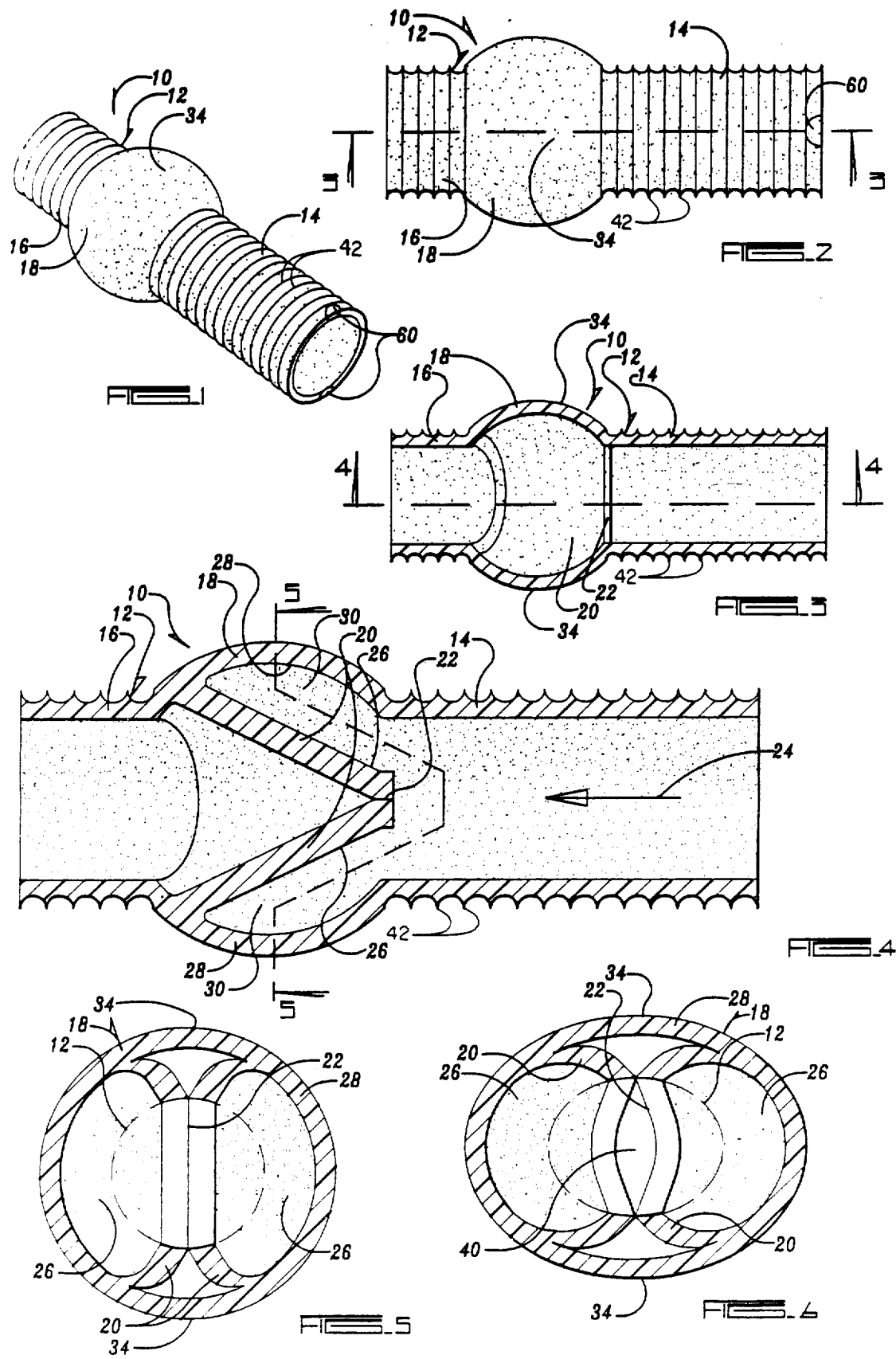

I claim:

1. The method of controlling urine flow in the urethra comprising the steps of;
   providing a tubular one way valve having a valve body with oppositely extending inlet and outlet tube portions, said valve body having converging blade valve elements normally closed to flow in one direction and being operable to flow in said one direction by application of external pressure on opposite sides of the valve body to open the valve elements,
   orienting the valve for insertion of said inlet tube portion into the urethra outlet orifice such that urine flow from the bladder to the outlet orifice of the urethra will be resisted,
   positioning the inlet tube portion of the valve in the outlet orifice of the urethra with the valve being remote to the bladder, and
   operating the valve to allow flow from the bladder through the valve by applying pressure on opposite sides of the valve body to spread the valve elements thereby allowing urine flow therethrough.

2. The method of claim 1 wherein the orientation of the valve includes orienting it such that it will be known by the user where the oppositely disposed pressure points on the valve body are located whereby during the operating step the pressure points may be quickly located and pressure applied without going through trial and error steps.

3. The method of claim 1 wherein the valve body is positioned entirely within the urethra outlet orifice of the male.

4. The method of claim 3 wherein during the operation step pressure is applied to the exterior of the penis at pressure points in alignment with the pressure points on the valve body.

5. The method of claim 1 wherein the inlet tube portion of the valve body is positioned in the orifice of the urethra of the female with the outer end of the valve body including the valve elements and pressure points being disposed in the labia majora to provide access to the pressure points on the valve body during the operation step.

6. A urethra urinary control valve comprising,
   an elongated tube having a cylindrical side wall with inner and outer ends, and serrations having edges forming annular lines are provided in the exterior of said tube side wall to restrict urine flow around the outside of said tube and holding the tube in the urethra, and a valve means positioned in said tube to restrict flow through said tube from said inner end to said outer end.

7. The structure of claim 6 wherein said valve is made from a silicone elastomer.

8. The structure of claim 6 wherein said valve means includes converging blade elements which are substantially flat at their outer free ends and engage each other along a straight line.

9. The structure of claim 6 wherein said tube includes inner and outer tube portions interconnected by an enlarged tube portion and said outer tube portion is adapted to be disposed in the urethra and extends from the fossa navicularis outwardly.

10. The structure of claim 6 wherein said valve means is disposed between said inner and outer ends of said tube whereby inner and outer tube portions are provided with said outer tube portion being adapted to be disposed in the labia majora and extending to adjacent the outer surface thereof.

11. The structure of claim 6 wherein indica is provided on the valve tube for orienting the valve when inserting it in the urethra such that it will be known where pressure is to be applied to open the valve means.

12. The method of controlling urine flow in the urethra comprising the steps of,
   providing a tubular one way valve having a valve body having valve elements normally closed to flow in one direction and being operable to flow in said one direction by application of external pressure on opposite sides of the valve body to open the valve elements,
   orienting the valve for insertion into the urethra such that urine flow from the bladder to the orifice of the urethra will be resisted,
   positioning the valve in the orifice of the urethra of the female with the outer end of the valve including the valve body and valve elements and pressure points being disposed in the labia majora to provide access to the pressure points on the valve body during operation, and
   operating the valve to allow flow from the bladder through the valve by applying pressure on opposite sides of the valve body to spread the valve elements thereby allowing urine flow therethrough.

13. A urethra urinary control valve comprising,
   an elongated tube having a cylindrical side wall with inner and outer ends, and serrations are provided on the exterior of said tube side wall to restrict urine flow around the outside of said tube when positioned in the urethra,
   a wedge shaped valve means positioned in said tube having converging blade elements oppositely disposed and integral with said side wall and extending laterally and longitudinally inwardly of said tube towards its inner end, said blade elements having free ends normally sealingly engaging each other to restrict flow through said tube from said inner end to said outer end, and
   said tube side wall including an enlarged portion extending rearwardly of said blade elements to provide enlarged oppositely disposed cavities between said blade elements and the adjacent enlarged tube side wall whereby urine in the forward end of said tube may collect in said enlarged cavities causing an increase in the pressure on said blade elements to maintain them in said closed position.

14. The structure of claim 13 wherein said serrations define edges forming annular lines to resist movement of said valve in said urethra.

15. The method of controlling urine flow in the urethra comprising the steps of, providing a tubular one way valve having a valve body having valve elements normally closed to flow in one direction and being operable to flow in said one direction by application of external pressure on opposite sides of the valve body to open the valve elements, orienting the valve for insertion into the urethra such that urine flow from the bladder to the orifice of the urethra will be resisted, positioning the valve in the orifice of the urethra with the outer end of the valve including the valve body and valve elements and pressure points being disposed outside of the urethra to provide access to the pressure points on the valve body during operation, and operating the valve to allow flow from the bladder through the valve by applying pressure on opposite sides of the valve body to spread the valve elements thereby allowing urine flow therethrough.

16. The method of controlling urine flow in the urethra comprising the steps of, providing a tubular one way valve having a valve body with oppositely extending inlet and outlet tube portions, said valve body having valve elements normally closed to flow in one direction and being operable to flow in said one direction by application of external pressure at pressure points on opposite sides of the valve body to open the valve elements, orienting the valve for insertion of said inlet tube portion into the urethra outlet orifice of the female with the outer end of the valve body including the valve elements and pressure points being disposed in the labia majora to provide access to the pressure points on the valve such that urine flow from the bladder to the outlet orifice of the urethra will be resisted, positioning the inlet tube portion of the valve in the outlet orifice of the urethra with the valve being remote to the bladder, and operating the valve to allow flow from the bladder through the valve by applying pressure on opposite sides of the valve body to spread the valve elements thereby allowing urine flow therethrough.

* * * * *

UNITED STATES PATENT AND TRADEMARK OFFICE
CERTIFICATE OF CORRECTION

PATENT NO. : 4,968,294　　　　　　　　　　　　　　　　　Page 1 of 2

DATED　　　 : Nov. 6, 1990

INVENTOR(S) : Fouad A. Salama

It is certified that error appears in the above-identified patent and that said Letters Patent is hereby corrected as shown below:

Sheet one of the drawings should be deleted to be replaced with the attached sheet one of drawings.

Signed and Sealed this

Fifth Day of February, 1991

*Attest:*

HARRY F. MANBECK, JR.

*Attesting Officer*　　　　　　　*Commissioner of Patents and Trademarks*